United States Patent [19]

Aramaki et al.

[11] Patent Number: 4,927,962

[45] Date of Patent: May 22, 1990

[54] PROCESS OF PREPARING FLUOROCARBON CARBOXYLIC OR SULFONIC ACID FROM ITS FLUORIDE

[75] Inventors: Minoru Aramaki; Hiroaki Sakaguchi; Tamio Nakamura, all of Ube, Japan

[73] Assignee: Central Glass Company, Limited, Ube, Japan

[21] Appl. No.: 237,072

[22] Filed: Aug. 29, 1988

[30] Foreign Application Priority Data

Aug. 31, 1987 [JP] Japan ............................ 62-215195
Aug. 31, 1987 [JP] Japan ............................ 62-215197
Sep. 29, 1987 [JP] Japan ............................ 62-242602

[51] Int. Cl.$^5$ .................... C07C 143/02; C07C 51/42
[52] U.S. Cl. .................................. 562/113; 562/119; 562/124; 562/593; 562/596; 562/605
[58] Field of Search .................. 260/513 H; 562/113, 562/119, 124, 593, 596, 605

[56] References Cited

U.S. PATENT DOCUMENTS 3,919,295 11/1975 Wechsberg et al. ............ 260/513 H

FOREIGN PATENT DOCUMENTS 304218 6/1955 Japan .
31268 1/1956 Japan .

OTHER PUBLICATIONS

Kogyo Kagaku Zasshi, 64, 1397–1400.

Primary Examiner—Alan Siegel
Attorney, Agent, or Firm—Fleit, Jacobson, Cohn, Price, Holman & Stern

[57] ABSTRACT

A fluorocarbon carboxylic acid $Rf(COOH)_m$ (Rf is $C_1$-$C_{10}$ perfluoroalkyl group, m is 1 or 2) is prepared by the steps of hydrolyzing $Rf(COF)_m$ with water to obtain an acidic solution, neutralizing the acidic solution with aqueous solution of KOH to form $Rf(COOK)_m$, precipitating and separating $Rf(COOK)_m$ from the solution and converting $Rf(COOK)_m$ into $Rf(COOH)_m$ by acid decomposition. The content of free fluorine can extremely be reduced by treating $Rf(COOK)_m$ with sulfuric acid and silica. The mother liquor is recycled after removing KF by treatment with a metal hydroxide and replenishing with KOH. In preparing a fluorocarbon sulfonic acid $RfSO_3H$ (Rf is $C_1$-$C_3$ perfluoroalkyl group) in substantially the same way, $RfSO_3K$ is formed in aqueous solution of KOH by bringing gaseous $RfSO_2F$ into contact with the KOH solution under normal pressure, while controlling the feed rate of $RfSO_2F$ per unit area of gas-liquid contact at a sufficiently low level.

12 Claims, No Drawings

PROCESS OF PREPARING FLUOROCARBON CARBOXYLIC OR SULFONIC ACID FROM ITS FLUORIDE

BACKGROUND OF THE INVENTION

This invention relates to a process of preparing a fluorocarbon carboxylic or sulfonic acid, viz., $Rf(COOH)_m$ or $RfSO_3H$ (Rf is a perfluoroalkyl group which may be saturated or unsaturated, and m is 1 or 2), from fluoride of the acid, $Rf(COF)_m$ or $RfSO_2F$.

Fluorocarbon carboxylic acids $Rf(COOH)_m$ having 1 to 10 carbon atoms in the Rf group are industrially important materials since simple derivatives of these acids have various uses. For example, some fluorocarbon carbonyl chlorides $Rf(COCl)_m$ are useful as intermediates of medicines and agricultural chemicals or polymerization initiators functioning at low temperatures, and excellent surfactants can be derived from $Rf(COOH)_m$ having a relatively large number of carbon atoms. Besides, some fluorocarbon compounds having special uses can easily be obtained by thermal decomposition of salts of $Rf(COOH)_m$. For example, thermal decomposition of $C_3F_7COOAg$ gives $C_6F_{14}$, which means dimerization of the perfluoroalkyl group, and thermal decomposition of $C_3F_7COONH_4$ gives a hydrogen-containing fluorocarbon $C_3F_7H$. The obtained fluorocarbons can be used as refrigerant or heat medium.

As to the preparation of $Rf(COOH)_m$, electrolytic fluorination is a generic method which does not need to be modified in fundamentals of apparatus and procedure according to the number of carbon atoms in the Rf group. JP No. 31-268 (1956) shows electrolytic fluorination of carbonyl chlorides or fluorides, $R(COF)_m$ or $R(COCl)_m$ (R is unsubstituted alkyl group corresponding to Rf) in anhydrous hydrogen fluoride. The reaction product, $Rf(COF)_m$, is recovered as a gas mixed with by-produced hydrogen or, when the product is high in boiling point, as a liquid which is separated from hydrogen fluoride and extracted from the bottom of the electrolytic cell. In general $Rf(COF)_m$ are readily soluble in water and rapidly undergo hydrolysis to form corresponding fluorocarbon carboxylic acids $Rf(COOH)_m$. In conventional processes a water scrubber is used to absorb $Rf(COF)_m$ in water and hydrolyze the absorbed fluoride, and the resultant aqueous solution is subjected to distillation for isolating the aimed $Rf(COOH)_m$.

In industrial practice of the above process, inconvenience is offered by the coexistence of a considerable quantity of HF with $Rf(COF)_m$ recovered from the electrolytic cell. It is impossible to drastically decrease the coexisting HF by merely devising equipment such as low temperature condenser and decanter. It is conceivable to remove the coexisting HF by passing the mixed gas through a tower packed with NaF, but this method is not suitable for industrial application because of high cost and problems about choking of the tower and regeneration of NaF. Furthermore, HF is formed by the hydrolyzing reaction of the carbonyl fluoride as represented by the equation (1), so that existence of HF in the obtained acid solution is inevitable.

$$Rf(COF)_m + H_2O \rightarrow Rf(COOH)_m + HF \quad (1)$$

Therefore, ordinary metal or glass materials are impracticable for the hydrolyzing and distillating apparatus, and it is necessary to use a very costly apparatus material such as a fluororesin lined material. Besides, complete removal of the coexisting HF is difficult even by distillation so that a problem arises as to purity of the obtained fluorocarbon carboxylic acid.

In preparing $Rf(COOH)_m$ having 1 to 5 carbon atoms in the Rf group by the above process, it is a matter of inconvenience for the final distillation operation that the boiling points of the aimed compounds are in the range of from 70° to 160° C. (e.g., $CF_3COOH$ 71° C., $n$-$C_3F_7COOH$ 119° C., $C_5F_{11}COOH$ 156° C.) and are not very far from the boiling point of water. For this reason it is necessary to remove a large quantity of water by using a very large-scale distillation tower and by consuming a large amount of energy.

Kogyo Kagaku Zasshi (a Japanese journal), 64, 1397 (1961) shows a process having the steps of forming a perfluoroalkylcarbonyl fluoride by electrolytic fluorination of an alcohol in anhydrous hydrogen fluoride, forcing the carbonyl fluoride to be absorbed in water followed by addition of silica and sodium carbonate, and separating sodium salt of the aimed fluorocarbon carboxylic acid by extraction with alcohol. In practice this process will not be economical because of including complicated operations for the solvent extraction and also because of requiring an isolation procedure such as distillation subsequent to the solvent extraction.

Fluorocarbon sulfonic acids $RfSO_3H$ having 1 to 3 carbon atoms in the Rf group are useful as catalysts for various reactions including Friedel-Crafts reactions, nitration reactions and polymerization reactions.

According to JP No. 30-4218 (1955), a fluorocarbon sulfonic acid of the above general formula is prepared from a corresponding sulfonyl fluoride. The fluoride, $RfSO_2F$, is obtained by electrolytic fluorination of a hydrocarbon sulfonyl chloride $RSO_2Cl$ (R is an unsubstituted alkyl group). The fluoride is gaseous at room temperature and, as a product of electrolytic fluorination, is diluted with a large quantity of hydrogen gas. Therefore the fluoride is first condensed by cooling to a sufficiently low temperature such as $-180°$ C., and the condensate is subjected to a hydrolyzing reaction with a KOH solution under pressure in an autoclave type reactor. This reaction is for converting the fluoride into potassium salt, $RfSO_3K$, and the desired $RfSO_3H$ is obtained by reacting $RfSO_3K$ with an excess quantity of nearly 100% sulfuric acid and distilling the reaction product.

However, in this process the condensation of $RfSO_2F$ is disadvantageous to industrial practice because very intense cooling has to be made at large expense of refrigerant or electric power for refrigeration and also because the operation is necessarily conducted batchwise. Besides, the hydrolysis of $RfSO_2F$ under pressure in an autoclave or the like entails high costs of equipment and operation. Because of including these inconvenient operations it is very difficult to conduct the overall process in a continuous manner, and inevitably the products become very costly.

SUMMARY OF THE INVENTION

It is an object of the present invention to provide an industrially favorable process for preparing fluorocarbon carboxylic acids $Rf(COOH)_m$ or fluorocarbon sulfonic acids $RfSO_3F$ at reduced costs of equipment and operation.

The present invention provides a process of preparing a fluorocarbon acid represented by the general formula Rf(ZH)$_m$, wherein Rf is a saturated or unsaturated perfluoroalkyl group having 1 to 10 carbon atoms, Z represents $CO_2$ or $SO_3$, and m is 1 or 2. The novel process comprises the steps of (a) treating a fluoride represented by the general formula Rf(Z'F)$_m$, wherein Z' is CO or $SO_2$, with water and KOH under normal pressure to thereby form a potassium salt represented by the general formula Rf(ZK)$_m$ in an aqueous solution of KOH; (b) precipitating the potassium salt from the aqueous solution and separating the precipitated potassium salt from the solution; (c) subjecting the separated potassium salt to acid decomposition to thereby convert the potassium salt into the fluorocarbon acid; (d) after the step (b) adding a hydroxide of a metal selected from alkali metals except potassium and alkaline earth metals to the aqueous solution to thereby precipitate fluoride of the metal and separating the precipitated fluoride from the solution; and (e) after the step (d) adding a complementary quantity of KOH to the aqueous solution and recycling the resultant KOH solution to the step (a).

In the case of preparing a fluorocarbon carboxylic acid Rf(COOH)$_m$ having 1 to 10 carbon atoms in the Rf group, the treatment at the initial step (a) comprises hydrolyzing a fluorocarbon carbonyl fluoride Rf(COF)$_m$ with water to thereby obtain an acidic aqueous solution and then mixing the acidic solution with an aqueous solution of KOH.

In the case of preparing a fluorocarbon sulfonic acid RfSO$_3$H having 1 to 3 carbon atoms in the Rf group, the treatment at the initial step (a) comprises bringing a gaseous fluorocarbon sulfonyl fluoride RfSO$_2$F into contact with an aqueous solution of KOH under normal pressure. At this step the feed rate of the sulfonyl fluoride to the KOH solution per unit area of gas-liquid contact is maintained not more than 0.5 mol/hr·m$^2$.

The process according to the invention includes no reaction or treatment that has to be conducted under high pressure, and the entire process can be performed in a continuous manner with recycle of the KOH solution. The process consists of relatively simple operations not using very costly apparatus, and either Rf(COOH)$_m$ or RfSO$_3$H of very high purity can be prepared at high yield.

DETAILED DESCRIPTION OF THE INVENTION

Perfluoroalkylcarbonyl fluorides Rf(COF)$_m$ for use in this invention in preparing fluorocarbon carboxylic acids are usually obtained by electrolytic fluorination of R(COF)$_m$ or R(COCl)$_m$ having corresponding alkyl groups (R), though any other method may alternatively be employed. The electrolytic fluorination method provides Rf(COF)$_m$ in gas form mixed with H$_2$ gas when the Rf group has not more than 4 carbon atoms and in liquid form when the Rf group has more than 4 carbon atoms. For example, in the case of n-C$_3$F$_7$COF the composition of the mixed gas delivered from the electrolytic cell is roughly as follows, assuming that the reflux condenser for recovering HF is maintained at $-35°$ C.

n-C$_3$F$_7$COF:3.3 vol %
C$_2$F$_5$COF:0.2 vol %
C$_3$F$_8$:6.2 vol %
COF$_2$:6.2 vol %
H$_2$O:74.2 vol %
HF:9.9 vol %

Such a mixed gas is subjected to hydrolysis by using a water scrubber to thereby form Rf(COOH)$_m$ together with HF. Simultaneously the coexisting COF$_2$ is hydrolyzed into CO$_2$ and HF, but CO$_2$ of this origin is easily purged from the reaction system since the hydrolyzing reaction liquid is acidic.

$$COF_2 + H_2O \rightarrow CO_2 + 2HF \qquad (2)$$

The hydrolysis can be carried out at any temperature below the boiling point of the resultant aqueous solution, but it is preferable to carry out absorption of the mixed gas in water at a temperature not higher than 40° C. in view of vapor pressures of HF and Rf(COOH)$_m$ formed by the hydrolysis.

An acid resistant synthetic resin represented by polytetrafluoroethylene is used in the water scrubber since acidic conditions are created therein. It is possible to use an alkali scrubber for absorption of the gases formed by the hydrolyzing reaction, but this is unfavorable because consumption of KOH increases by reaction with CO$_2$ originating from COF$_2$ to form potassium carbonate and also because the purity of subsequently precipitated Rf(COOK)$_m$ lowers by intrusion of potassium carbonate.

The next operation is neutralizing the acidic aqueous solution obtained by the above operation. In this invention an aqueous solution of KOH is used as an alkaline neutralizing solution, whereby Rf(COOH)$_m$ and HF in the acidic solution are converted into Rf(COOK)$_m$ and KF, respectively. The temperature of the alkali solution is arbitrary, though it should be lower than the boiling point.

KOH is an alkali readily available as an industrial material, and an important advantage of using KOH in this invention resides in that KF formed by the neutralizing operation has very high solubility in water (0.92 kg KF/kg H$_2$O at 18° C.), whereas fluorides of other metals are generally low in solubility in water. When NaOH is used for the neutralizing purpose, HF is converted into NaF. The solubility of NaF in water (0.04 kg/kg H$_2$O at 25° C.) is far lower than that of KF, and actual solubility of NaF becomes still lower by the salting-out effect of Rf(COONa)$_m$. Therefore, it is inevitable that a considerable amount of precipitated NaF mingles with Rf(COONa)$_m$ as a cause of lowering of purity of the final product.

Rf(COOK)$_m$ generally have good solubilities in water, and higher solubilities with less carbon atoms. However, the solubility of every Rf(COOK)$_m$ greatly decreases as the concentration of coexisting KOH increases. For example, at normal temperature the solubility of n-C$_3$F$_7$COOK is more than 3 kg/kg H$_2$O in the absence of KOH but decreases to only 0.1 kg/kg H$_2$O in the presence of 0.43 kg of KOH in 1 kg of H$_2$O. One way to precipitate Rf(COOK)$_m$ from the neutralized aqueous solution is further adding KOH to the solution. However, the best way is concentrating the aqueous solution to increase the concentration of Rf(COOK)$_m$ as well as the concentration of KOH. The concentration can be accomplished by a usual heat evaporation method using an evaporator made of a common material such as ordinary steel or stainless steel, and for the sake of promotion it is optional to carry out evaporation under reduced pressure or with blow of a carrier gas.

It is possible to precipitate the potassium carboxylate during the evaporation operation, but it is preferable to cool the concentrated solution because a larger amount of precipitate is obtained in a form convenient for the succeeding filtration operation. From the concentrated and cooled solution the potassium salt precipitates as crystals of 0.1 to 2 or 3 mm, which can easily be filtered out by centrifugal filtration or suction filtration or by almost any other filtration method. In particular centrifugal filtration gives a cake containing only about 5 wt % of water, so that the cake does not need to be washed with water.

Starting from the mixed gas of the composition shown hereinbefore by way of example, a cake of the following composition (typical) is obtained.

n-$C_3F_7$COOK: 86.0 wt %
$C_2F_5$COOK: 4.9 wt %
KF: 3.1 wt %
KOH: 1.0 wt %
$H_2O$: 5.0 wt %

As to purity of the potassium salt it suffices to merery dry the cake of the above composition. Although KF and KOH are contained, the presence of such small amounts of impurities is hardly obstructive to the subsequent acid decomposition of the potassium carboxylates. If necessary it is possible to almost completely remove KF with little dissolution of the carboxylates by washing the cake with an aqueous solution rich in potassium ion, such as a KOH solution.

$Rf(COOK)_m$ formed and separated by the above operations can easily be converted into $Rf(COOH)_m$ by decomposition with sulfuric acid. By distillation the aimed $Rf(COOH)_m$ is isolated from the reaction liquid containing sulfuric acid.

In advance of the acid decomposition reaction, it is possible to extremely reduce the content of free fluorine in $Rf(COOK)_m$ by treating the carboxylate with sulfuric acid and silica or a source of silica such as a silicate containing substance. In the presence of sulfuric acid, free fluorine contained in the potassium salt reacts with silica and turns into $SiF_4$ gas which can easily be dissipated from the treated material. By making this treatment the content of free fluorine in the final product, $Rf(COOH)_m$ can be reduced to less than 1 ppm.

$$SiO_2 + 4HF \rightarrow 2H_2O + SiF_4 \uparrow \qquad (3)$$

It is desirable to use 80% or more concentrated sulfuric acid, and it is suitable that the quantity of sulfuric acid is not less than equivalent to the carboxylate subjected to treatment and not more than 3 times the equivalent. If the quantity of sulfuric acid is insufficient for well mixing with the carboxylate the reaction of free fluorine will remain incomplete. On the other hand, use of a large excess of sulfuric acid does not appreciable augment the defluorinating effect.

Examples of silicate substances that can be used in place of silica are diatomaceous earth, sodium silicate and some glasses. It is suitable that the quantity of silica is 4 to 20 times as large as the theoretical quantity according to the equation (3). If the quantity of silica is smaller the expected reaction will remain incomplete. On the other hand, use of a still larger excess of silica does not appreciably improve the result of defluorinating treatment.

The defluorinating treatment can be made even at room temperature, but it is preferable to carry out this treatment at 80°–150° C. for 0.5–6 hr with continuous stirring. The treatment can be made at normal pressure, but preferably the treatment is made under reduced pressure to promote dissipation of fluorine as $SiF_4$ gas.

Also it is effective to blow a carrier gas such as air or nitrogen gas into the slurry under reaction.

The description turns to the mother liquor left as filtrate after separating precipitated $Rf(COOK)_m$. The mother liquor contains KOH and small amounts of $Rf(COOK)_m$ as useful materials together with unwanted KF. We have found and confirmed that KF can efficiently be removed from the mother liquor by utilizing a double decomposition reaction represented by the following equation.

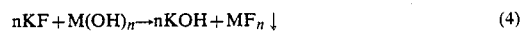

$$nKF + M(OH)_n \rightarrow nKOH + MF_n \downarrow \qquad (4)$$

wherein M is a metal which forms a fluoride insoluble or low in solubility in water, and n is the valence of the metal M.

For industrial practice it is suitable to select the metal M from alkali metals and alkaline earth metals, in particular from Na, Li, Mg and Ca. That is, the removal of KF can be accomplished by using a metal hydroxide cheaper than KOH. Furthermore, this reaction gives KOH which is an indispensable material in the process of the invention. Since the above reaction is carried out in the presence of a large amount of KOH, the solubility of the metal fluoride formed by the reaction becomes practically null. For example, NaF formed by using NaOH as the metal hydroxide has a solubility of about 0.04 kg/kg $H_2O$ in pure water, but the solubility decreases to only 0.0016 kg/kg $H_2O$ when 0.52 kg of KOH is contained in 1 kg of water. Therefore, almost stoichiometrical defluorination can be accomplished.

The double decomposition reaction proceeds even at room temperature, but it is preferable to carry out the reaction at a temperature not lower than 60° C. to prevent precipitation of $MF_n$ as fine crystals inconvenient for separation by filtration. It is suitable that the quantity of $M(OH)_n$ used in this reaction is approximately theoretical (with respect to fluorine ion in the mother liquor) or less than theoretical. Addition of a more than theoretical quantity of $M(OH)_n$ results in precipitation of undesirably fine crystals of $MF_n$, and a portion of $MF_n$ will remain in the treated mother liquor and intrude into $Rf(COOK)_m$ when the mother liquor is reused as the alkali solution for neutralizing the acidic solution obtained by the hydrolysis at the initial stage of the process. It is desirable that the fluorine ion concentration in the mother liquor to be defluorinated is not more than 100 g/l because there is a tendency toward an increase in the amount of fine crystals of precipitated $MF_n$ when the concentration of fluorine ion in the treated solution is too high.

If fine crystals of $MF_n$ are formed, it is possible to grow the crystals to the extent of convenience for filtration by heating the treated mother liquor at a temperature ranging from about 80° C. to the boiling point for at least 1 hr and preferably for 2–15 hr.

After removing KF by the above treatment, complementary quantities of KOH and water are added to the mother liquor to recycle it to the stage of neutralizing the acidic solution obtained by hydrolysis.

The above description of the preparation of $Rf(COOH)_m$ from gaseous $Rf(COF)_m$ is applicable also to the case of using a liquid $Rf(COF)_m$ without any substantial difference. The sole difference is simply adding the liquid fluoride to water instead of forcing the gaseous fluoride to be absorbed in water.

The following are nonlimitative examples illustrative of the preparation of fluorocarbon carboxylic acids by the method according to the invention.

EXAMPLE 1

An electrolytic fluorination operation was carried out by continuously introducing 110 g/hr of n-$C_3H_7COCl$ and 310 g/hr of anhydrous hydrogen fluoride into an electrolytic cell under the following conditions: cell temperature 15° C.; voltage and current 5.5 V and 500 A; reflux condenser temperature −35° C. A mixed gas of the following composition was obtained at a rate of 420 g/hr.

|  | weight (g) | wt % | vol % |
|---|---|---|---|
| n-$C_3F_7COF$ | 90.7 | 21.7 | 3.3 |
| $C_2F_5COF$ | 4.7 | 1.1 | 0.2 |
| $C_3F_8$ | 146.7 | 35.0 | 6.2 |
| $COF_2$ | 51.5 | 12.3 | 6.2 |
| $H_2$ | 18.7 | 4.5 | 74.2 |
| HF | 107.4 | 25.5 | 9.9 |
| total | 419.7 | 100.0 | 100.0 |

In a water scrubber packed with Tellerette of polyethylene the mixed gas was first hydrolyzed with water (600 g per 419.7 g of the mixed gas) to give an acid solution of the following composition, and then the acid solution was subjected to neutralizing reaction with a KOH solution (a recycled solution of the following composition) which was supplied at 30° C. to the scrubber at a rate of 2.1 kg/hr.

| Acid Solution Obtained by Hydrolysis | | |
|---|---|---|
|  | weight (g) | wt % |
| n-$C_3F_7COOH$ | 89.9 | 11.1 |
| $C_2F_5COOH$ | 4.6 | 0.5 |
| HF | 147.6 | 17.9 |
| $H_2O$ | 577.9 | 70.5 |
| total | 820.0 | 100.0 |

| KOH Solution | | |
|---|---|---|
|  | weight (g) | wt % |
| n-$C_3F_7COOK$ | 6.0 | 0.3 |
| KF | 60.0 | 2.8 |
| KOH | 589.0 | 27.5 |
| $H_2O$ | 1489.0 | 69.4 |
| total | 2144.0 | 100.0 |

The neutralizing reaction gave a carboxylate solution of the following composition, which was extracted from the scrubber at a rate of 2.9 kg/hr. At the gas outlet of the scrubber, no trace of n-$C_3F_7COF$ was detected in the discharging gas.

| Neutralized Carboxylate Solution | | |
|---|---|---|
|  | weight (g) | wt % |
| n-$C_3F_7COOK$ | 112.0 | 3.8 |
| $C_2F_5COOK$ | 6.0 | 0.2 |
| KF | 489.0 | 16.5 |
| KOH | 150.0 | 5.1 |
| $H_2O$ | 2208.0 | 74.5 |
| total | 2965.0 | 100.0 |

Next, in a stainless steel evaporator using steam as heating means, 236.5 kg of the above neutralized solution was heated to its boiling point until evaporation of 88.8 kg of water. Cooling of the remaining liquid to 30° C. caused precipitation of crystals 0.3 to 1 mm in size. The resultant slurry was filtered with a centrifugal separator, and the separated solid matter was washed with 12 kg of 36 wt % KOH solution and dried at 120° C. for 10 hr to obtain 11.6 kg of a crystalline powder. By analysis, this powder consisted of 91.4 wt % of n-$C_3F_7COOK$, 5.1 wt % of $C_2F_5COOK$, 0.3 wt % of KF, 2.9 wt % of KOH and 0.3 wt % of $H_2O$.

Next, 11.6 kg of this crystalline powder was mixed with 10.7 kg of 98% sulfuric acid and 40 g of active silica powder, and the resultant slurry was kept heated at 100° C. and stirred for 5 hr under reduced pressure of 15 Torr, while nitrogen gas was continuously blown into the slurry to promote dissipation of $SiF_4$ gas formed by the reaction. After this treatment the reaction liquid was distilled to obtain refined n-$C_3F_7COOH$. The obtained acid had purity of 99.98%, contained 200 ppm of moisture and was less than 1 ppm in the content of free fluorine.

As a defluorinating treatment of the mother liquor separated by the aforementioned centrifugal filtration, 89.6 kg of an aqueous slurry containing 30 wt % of $Ca(OH)_2$ was added to 135 kg of the mother liquor kept heated at 100° C. to cause precipitation of crystals of $CaF_2$. Removing the precipitate with a filter press, 174 kg of a defluorinated alkali solution of the following composition was obtained. The filtration gave a cake which weighed 50.8 kg and consisted of 28.3 kg (55.7 wt %) of $CaF_2$, 0.7 kg (1.3 wt %) of KF, 6.4 kg (12.7 wt %) of KOH and 15.4 kg (30.3 wt %) of $H_2O$.

| Defluorinated Mother Liquor (parenthesized values: before the defluorinating treatment) | | | |
|---|---|---|---|
|  | weight (kg) |  | wt % |
| n-$C_3F_7COOK$ | 0.6 | (0.6) | 0.3 | (0.4) |
| KF | 5.7 | (48.5) | 3.3 | (35.8) |
| KOH | 49.2 | (14.9) | 28.2 | (11.1) |
| $H_2O$ | 118.7 | (71.4) | 68.2 | (52.7) |
| total | 174.2 | (135.4) | 100.0 | (100.0) |

By adding complementary quantities of KOH and water the defluorinated mother liquor could be reused as the KOH solution for neutralizing the acid solution obtained by the initial hydrolyzing treatment.

EXAMPLE 2

First, 2 kg of a mixture of $CF_3(CF_2)_6COF$ (95 wt %) and HF (5 wt %) was mixed with 0.6 liter of water by stirring. The mixture was mixed with 2.4 liters of a KOH solution containing 500 g/l of KOH, and the resultant mixture was kept heated at 80° C. under reflux for 30 min. After that the reaction liquid was heated to its boiling point until evaporation of 1.6 kg of water. The remaining liquid was cooled to 30° C., which caused precipitation of crystals. The precipitate was separated by centrifugal filtration and washed with 1000 g of 36% KOH solution, followed by drying. The dried crystalline powder weighed 2.095 kg and contained 2.020 kg (96.4 wt %) of $CF_3(CF_2)_6COOK$, 0.006 kg (0.3 wt %) of KF, 0.063 kg (3.0 wt %) of KOH and 0.006 kg (0.3 wt %) of $H_2O$.

The entire quantity of the crystalline powder was mixed with 1.1 kg of 98% sulfuric acid and 8 g of active silica powder, and the resultant slurry was kept heated at 150° C. and stirred for 3 hr under reduced pressure of 15 Torr, while nitrogen gas was continuously blown into the slurry to promote dissipation of SiF$_4$ gas formed by the reaction. After this treatment the reaction liquid was distilled to obtain CF$_3$(CF$_2$)$_6$COOH of more than 99.9% purity as distillate. In the obtained acid the content of moisture was 200 ppm, and the content of free fluorine was less than 1 ppm.

The following description relates to the preparation of fluorocarbon sulfonic acids.

Perfluoroalkylsulfonyl fluorides RfSO$_2$F for use in this invention are usually obtained by electrolytic fluorination of RSO$_2$F or RSO$_2$Cl having corresponding alkyl groups (R), though this is not limitative. In the case of using RSO$_2$F the sole impurity to be taken care of is HF used as the fluorinating agent. In the case of RSO$_2$Cl, not only HF accompanying RfSO$_2$F but also HCl and HClO formed by the electrolytic fluorination have to be removed. Most of HF is returned from a reflux condenser provided at the outlet of the electrolytic cell, but a portion of HF is discharged from the cell. It is possible to remove most of the halogen compounds mixed with RfSO$_2$F by absorption in a water scrubber. As a matter of convenience, RfSO$_2$F are hardly absorbed in water and particularly in acidic aqueous solution. When water is used as absorbent, it is suitable to carry out the absorption of the impurities at a temperature not higher than 40° C. in view of vapor pressures of HF, HCl and HClO. Furthermore, vapor pressures of these impurities can be suppressed and, hence, the absorbing efficiency can be improved by using a dilute aqueous solution of an alkali as absorbent having the function of continuously neutralizing the absorbed acidic impurities. RfSO$_2$F are hardly absorbed in alkaline aqueous solutions. The alkali is selected from hydroxides and oxides of alkali metals and alkaline earth metals such as Na, K, Li, Ca and Mg, and the alkali concentration in the aqueous solution is at least 0.1 g/l and preferably in the range from 1 to 2 g/l. The absorption of the impurities in an alkaline solution can be carried out in an ordinary absorption tower such as a wetted wall tower or a packed tower. The absorbing efficiency can be enhanced by cooling the absorbing solution, but the purpose can fully be accomplished even at normal temperature. By using an alkaline absorbing solution it is possible to obtain RfSO$_2$F almost free of impurities, so that RfSO$_3$K of very high purity can be obtained at the initial step of the process according to the invention.

The initial step is bringing RfSO$_2$F into contact with an aqueous solution of KOH to hydrolyze the sulfonyl fluoride into sulfonate RfSO$_3$K. According to the prior art, RfSO$_2$F in the form of condensate is reacted with a KOH solution under pressure in an autoclave. This is because at normal pressure the rate of hydrolysis of RfSO$_2$F in a KOH solution is very low. Using an ordinary scrubber such as a wetted wall tower or a packed tower it was very difficult to hydrolyze a substantial part of RfSO$_2$F supplied in gas form, and the yield of RfSO$_3$K was 20-30% at best.

Regarding absorption of gaseous RfSO$_2$F in an aqueous alkaline solution at normal pressure, we have discovered that the efficiencies of absorption and hydrolysis are remarkably improved by greatly enlarging the surface area of the absorbing liquid per unit quantity of the supplied gas. In other words, the feed rate of the gas per unit area of gas-liquid contact is limited to a very low level. By doing so, it has become possible to accomplish almost complete absorption and hydrolysis of the supplied gaseous RfSO$_2$F. For example, in the case of contacting gaseous CF$_3$SO$_2$F with a KOH solution, the yield of CF$_3$SO$_3$K becomes about 65% when the feed rate of CF$_3$SO$_2$F per unit area of gas-liquid contact, G, is controlled to 0.5 mol/hr·m$^2$, and the absorption and hydrolysis proceed almost stoichiometrically when G is controlled to 0.15 mol/hr·m$^2$ or below.

Another important factor is the temperature of the alkaline solution. The liquid temperature should not be lower than room temperature, and it is best for the efficiency of absorption to maintain the liquid temperature within the range from 60° to 90° C. The efficiency of absorption is not further enhanced by raising the liquid temperature beyond 90° C. because of a sharp rise in vapor pressure of water.

As the alkali it is suitable to use a potassium salt since KF is far higher in solubility in water than other metal fluorides, and KOH is selected in view of generation of obstructive gases from other popular potassium salts such as KHCO$_3$ and K$_2$CO$_3$. In the aqueous solution of KOH for use as the absorbing and hydrolyzing liquid, the alkali concentration should be at least 5 g/l and preferably ranges from 70 to 300 g/l. The gas-liquid contact is carried out in a scrubber, and a scrubber of a packed tower type is preferred. The packing may be of any type insofar as it is sufficiently large in surface area as represented by Raschig rings.

Under the above described conditions it is possible to accomplish continuous hydrolysis of RfSO$_2$F (having 1 to 3 carbon atoms in the Rf group) in an alkali scrubber under normal pressure. The hydrolyzing reaction is expressed in the following manner.

$$RfSO_2F + 2KOH \rightarrow RfSO_3K + KF + H_2O \qquad (5)$$

RfSO$_3$K generally have high solubilities in water. For example, about 1 kg of CF$_3$SO$_3$K dissolves in 1 kg of water at normal temperature. However, the solubility of every RfSO$_3$K greatly decreases when a potassium salt, in particular KOH, is added to the water. For example, when the concentration of KOH is 0.83 kg/kg H$_2$O only 0.09 kg of CF$_3$SO$_3$K dissolves in 1 kg of water. Besides, solubilities of RfSO$_3$K greatly depend on temperature and increase at higher temperatures.

Considering such tendencies of solubilities of RfSO$_3$K, an effective way to precipitate RfSO$_3$K from the aqueous solution obtained at the initial step is further adding KOH to the solution. Another and probably more favorable way is partly evaporating water in the solution by heating the solution under normal pressure or reduced pressure to sufficiently increase the concentration of RfSO$_3$K as well as the concentration of potassium ion and then cooling the solution. By such treatment RfSO$_3$K precipitates as crystals of 0.1 to 2 or 3 mm, which can easily be filtered out by centrifugal filtration, suction filtration or by almost any other filtration method. In particular centrifugal filtration gives a cake containing only about 5 wt % of water, so that RfSO$_3$K of more than 95% purity is obtained by simply drying the cake. Although KF and KOH are contained, the presence of small amounts of these impurities is hardly obstructive to the subsequent acid decompositin of the potassium sulfonates. If necessary it is possible to almost completely remove KF with little dissolution of the sulfonates by washing the cake with an aqueous solution rich in potassium ion, such as a KOH solution.

RfSO$_3$K formed and separated in powder form by the above operations can easily be converted in to RfSO$_3$H by decomposition with sulfuric acid. By distillation the aimed $RfSO_3H$ is isolated from the reaction liquid containing sulfuric acid. Since $RfSO_3H$ have relatively high boiling points (e.g., b.p. of $CF_3SO_3H$ is 162° C.), it is suitable to isolate the aimed acid by distillation under reduced pressure.

In advance of the acid decomposition reaction, it is possible to extremely reduce the content of free fluorine in $RfSO_3K$ by treating the sulfonate with sulfuric acid and silica or a silicate containing substance, as described hereinbefore with respect to the preparation of fluorocarbon carboxylic acids. By such treatment the content of free fluorine in the finally obtained $RfSO_3H$ can be reduced to less than 1 ppm.

The description turns to the mother liquor left as filtrate after separating precipitated $RfSO_3K$. The mother liquor contains KOH and small amounts of $RfSO_3K$ as useful materials together with unwanted KF. As described hereinbefore with respect to the preparation of $Rf(COOH)_m$, KF in the mother liquor is removed by utilizing a double decomposition reaction represented by the equation (4). The conditions of this reaction are as described hereinbefore. Also in this case it is undesirable to use a more than theoretical quantity of metal hydroxide $M(OH)_n$ because, besides the disadvantages described hereinbefore, recycling of the treated KOH solution to the scrubber may cause choking of the scrubber by precipitation of $MF_n$.

After removing KF by the above treatment, complementary quantities of KOH and water are added to the mother liquor to recycle it to the stage of hydrolyzing $RfSO_2F$.

The following nonlimitative examples illustrate the preparation of fluorocarbon sulfonic acids by the method according to the invention.

EXAMPLE 3

An electrolytic fluorination operation was carried out by continuously introducing 289 g/hr of $CH_3SO_2Cl$ and 320 g/hr of anhydrous hydrogen fluoride into an electrolytic cell under the following conditions: cell temperature 10° C.; voltage and current 5.5 V and 500 A; reflux condenser temperature −40° C. A mixed gas of the following composition was obtained at a rate of 609 g/hr.

|  | weight (g) | wt % | vol % |
| --- | --- | --- | --- |
| $CF_3SO_2F$ | 306.6 | 50.3 | 13.7 |
| HF | 98.4 | 16.2 | 7.6 |
| $Cl_2$ | 89.5 | 14.7 | 8.6 |
| $CF_4$ | 44.4 | 7.3 | 3.4 |
| $H_2$ | 18.7 | 3.1 | 63.3 |
| others | 51.4 | 8.4 | 3.4 |
| total | 609.0 | 100.0 | 100.0 |

In a scrubber having a liquid surface area of 0.01 m² per liter of gas, the mixed gas was washed with 0.1 wt% aqueous solution of NaOH at 30° C. to completely remove HF and $Cl_2$. The washed gas was introduced into a steel scrubber packed with Raschig rings made of stainless steel, while A KOH solution heated to 70° C. was continuously supplied to the scrubber to absorb the gas and hydrolyze the contained sulfonic acid fluoride. The feed rate of the gas per unit area of gas-liquid contact, G, was controlled to 0.15 mol/hr.m². The KOH solution was a recycled solution of the following composition, and the feed rate of this solution was 2.9 kg/hr.

| KOH Solution for Gas Absorption | | |
| --- | --- | --- |
|  | weight (g) | wt % |
| $CF_3SO_3K$ | 60 | 2.1 |
| KF | 12 | 0.4 |
| KOH | 450 | 15.5 |
| $H_2O$ | 2380 | 82.0 |
| total | 2902 | 100.0 |

By absorbing the gas and hydrolyzing the sulfonic acid fluoride contained in the gas the KOH solution turned into a sulfonate solution of the following composition, which was extracted from the scrubber at a rate of 3.2 kg/hr. At the gas outlet of the scrubber, no trace of $CF_3SO_2F$ was detected in the discharging gas.

| Obtained Sulfonate Solution | | |
| --- | --- | --- |
|  | weight (g) | wt % |
| $CF_3SO_3K$ | 439 | 13.7 |
| KF | 129 | 4.0 |
| KOH | 224 | 7.0 |
| $H_2O$ | 2416 | 75.3 |
| total | 3208 | 100.0 |

Next, in a stainless steel evaporator using steam as heating means, 32 kg of the above sulfonate solution was heated to its boiling point until evaporation of 1.88 kg of water. Cooling of the remaining liquid to 30° C. caused precipitation of crystals 0.5 to 1 mm in size and hence convenient for filtration. The resultant slurry was filtered with a centrifugal separator, and the separated solid matter was dried at 120° C. for 10 hr to obtain 3.95 kg of a crystalline powder of the following composition.

| Crude Sulfonate Crystals | | |
| --- | --- | --- |
|  | weight (g) | wt % |
| $CF_3SO_3K$ | 3790 | 96.0 |
| KF | 50 | 1.2 |
| KOH | 80 | 2.0 |
| $H_2O$ | 30 | 0.8 |
| total | 3950 | 100.0 |

Next, 3 kg of this crystalline powder was mixed with 1.05 kg of 98% $H_2DO_4$ and 1.9 kg of 26% fuming sulfuric acid, and the mixture was stirred at 120° C. for 1 hr to thereby accomplish acid decomposition of the potassium sulfonate. After that the reaction liquid was subjected to simple distillation under reduced pressure of 40–25 Torr. As a distillate at 130°–110° C., 2.32 kg of $CF_3SO_3H$ of more than 99% purity was obtained. In this product the content of free fluorine was 0.5%.

Another portion of the crystalline powder was treated in a different way for extreme reduction in the content of free fluorine in the final product. In this case 3 kg of the crystalline powder was mixed with 2.0 kg of 98% $H_2SO_4$ and 40 g of active silica powder, and the resultant slurry was kept heated at 150° C. and stirred for 3 hr under reduced pressure of 15 Torr, while nitrogen gas was continuously blown into the slurry to promote dissipation of $SiF_4$ gas formed by the reaction. After this treatment the reaction liquid was distilled in the above described manner. In $CF_3SO_3H$ obtained as distillate, the content of free fluorine was less than 1 ppm.

As an experimental defluorinating treatment of the mother liquor separated by the aforementioned centrifugal filtration, 160 g of 48 wt% NaOH solution was added to 917 g of the mother liquor kept heated at 90°–100° C. to cause the precipitation of crystals of NaF. Removing the precipitate by filtration, 982 g of a solution of the following composition was obtained. This test confirmed that by adding complementary quantities of KOH and water the defluorinated mother liquor could be reused as the gas absorbing solution in the alkali scrubber.

| Defluorinated Mother Liquor | | |
|---|---|---|
| | weight (g) | wt % |
| $CF_3SO_3K$ | 60 | 6.1 |
| KF | 12 | 1.2 |
| KOH | 319 | 32.5 |
| $H_2O$ | 591 | 60.2 |
| total | 982 | 100.0 |

EXAMPLE 4

Vapor of 202 g of $C_2F_5SO_2F$ was introduced into a steel scrubber packed with Raschig rings of stainless steel, while 30 wt% aqueous solution of KOH heated to 70° C. was circulatorily pumped into the scrubber. The feed rate of the sulfonyl fluoride vapor, in terms of G, was controlled to 0.4 mol/hr.m². The absorption of the vapor in the KOH solution and the hydrolysis of the absorbed vapor gave an aqueous solution in which amounted to 1322 g in total and consisted of 238 g of $C_2F_5SO_3K$, 224 g of KOH, 58 g of KG and 802 g of water.

The obtained solution was heated to its boiling point until evaporation of 402 g of water, and the remaining liquid was cooled to 30° C. to cause precipitation of crystals 0.5 to 1 mm in size. The precipitate was separated by suction filtration and was dried to obtain 230 g of a crystalline powder, which consisted of 223.1 g (97.0 wt%) of $C_2F_5SO_3K$, 5.5 g (2.4 wt%) of KOH and 1.4 g (0.6 wt%) of KF. Acid decomposition of this sulfonate powder and distillation of the reaction product were performed in the same manner as in Example 3. As the result $C_2F_5SO_3H$ of more than 99% purity was obtained.

The mother liquor left as the filtrate of the aforementioned suction filtration was 680 g of aqueous solution, which consisted of 14.9 g (2.2 wt%) of $C_2F_5SO_3K$, 218.5 g (32.1 wt%) of KOH, 56.6 g (8.3 wt%) of KF and 390 g (57.4wt%) of $h_2O$. To this solution 39 g of NaOH was added and the solution was stirred, which caused precipitation of a crystalline substance. The precipitate was separated by filtration and was washed with 20 g of water and dried to thereby obtain 34 g of NaF. After this treatment, the mother liquid weighed 699 g and consisted of 14.9 (2.1 wt%) of $C_2F_5SO_3K$, 273.1 g (39.1 wt%) of KOH, 1.0 g (0.1 wt%) of NaF and 410 g (58.7 wt%) of $H_2O$.

What is claimed is:

1. A process of preparing a fluorocarbon carboxylic acid represented by the formula $Rf(COOH)_m$, wherein Rf is a saturated or unsaturated perfluoroalkyl group having 1 to 10 carbon atoms, and m is 1 or 2, the process comprising the steps of:
    (a) hydrolyzing a fluorocarbon carbonyl fluoride represented by the formula $Rf(COF)_m$ with water to thereby obtain an aqueous solution of said fluorocarbon carboxylic acid;
    (b) mixing said aqueous solution with an aqueous solution of KOH to thereby obtain an aqueous solution in which a potassium salt of said fluorocarbon carboxylic acid is dissolved together with KF;
    (c) partly evaporating water of the aqueous solution obtained at step (b) and thereafter cooling the solution to thereby precipitate said potassium salt from the solution and separating said potassium salt from the solution;
    (d) adding a hydroxide of a metal selected from the group consisting of alkali metals except potassium and alkaline earth metals to the aqueous solution from which said potassium salt was separated to cause formation of KOH and precipitation of fluoride of said metal by reaction of said KF with said hydroxide and separating the precipitated fluoride from the solution;
    (e) adding KOH to the aqueous solution from which the metal fluoride was separated and recycling the resultant aqueous solution of KOH to step (b); and
    (f) subjecting the separated potassium salt obtained in step (c) to acid decomposition to thereby convert the potassium salt into said fluorocarbon carboxylic acid.

2. A process according to claim 1, wherein the hydrolysis at step (a) is carried out at a temperature not lower than 40° C.

3. A process according to claim 1, wherein sulfuric acid is used for the acid decomposition at step (f).

4. A process according to claim 1, further comprising the step of treating the potassium salt separated at step (c) with sulfuric acid and silica or a source of silica to thereby remove free fluorine from the potassium salt prior to step (f).

5. A process according to claim 1, further comprising the step of recovering said fluorocarbon carboxylic acid from the product of the acid decomposition reaction at step (f) by distillation.

6. A process of preparing a fluorocarbon sulfonic acid represented by the formula $RfSO_3H$, wherein Rf is a saturated or unsaturated perfluoroalkyl group having 1 to 3 carbon atoms, the process comprising the steps of:
    (a) bringing a gaseous fluorocarbon sulfonyl fluoride represented by the formula $RfSO_2F$ into contact with an aqueous solution of KOH under normal pressure to thereby obtain an aqueous solution in which the potassium salt of said fluorocarbon sulfonic acid is dissolved together with KF, the feed rate of said fluoride to said solution per unit area of gas-liquid contact being maintained at not more than 0.5 mol/hr 7²;
    (b) partly evaporating water of the aqueous solution obtained at the step (a) and thereafter cooling the solution to thereby precipitate said potassium salt from the solution and separating the precipitated potassium salt from the solution;
    (c) adding a hydroxide of a metal selected from the group consisting of alkali metals except potassium and alkaline earth metals to the aqueous solution from which said potassium salt was separated to cause formation of KOH and precipitation of fluoride of said metal by reaction of said KF with said hydroxide and separating the precipitated metal fluoride from the solution;

(d) adding KOH to the aqueous solution from which said metal fluoride was separated and recycling the resultant KOH solution to the step (a); and (e) subjecting the separated potassium salt of said fluorocarbon sulfonic acid obtained in step (b) to acid decomposition to thereby convert said potassium salt into said fluorocarbon sulfonic acid.

7. A process according to claim 6, wherein at step (a) said feed rate of said fluoride is maintained not more than 0.15 mol/hr.m$^2$.

8. A process according to claim 6, wherein at step (a) the temperature of the KOH solution is in the range from 60° to 90° C.

9. A process according to claim 6, wherein at step (a) the alkali concentration in the KOH solution is in the range from 70 to 300 g/l.

10. A process according to claim 6, wherein sulfuric acid is used for the acid decomposition at step (e).

11. A process according to claim 6, further comprising the step of treating the potassium salt separated at step (b) with sulfuric acid and silica or a source of silica to thereby remove free fluorine from the potassium salt prior to step (e).

12. A process according to claim 6, further comprising the step of recovering said fluorocarbon sulfonic acid from the product of the acid decomposition reaction at step (e) by distillation.

* * * * *